United States Patent [19]  [11] Patent Number: 4,929,070
Yokota et al.  [45] Date of Patent: May 29, 1990

[54] ILLUMINATION OPTICAL SYSTEM FOR ENDOSCOPES

[75] Inventors: Akira Yokota; Masao Kuga, both of Hachiouji, Japan

[73] Assignee: Olympus Optical Co. Ltd., Tokyo, Japan

[21] Appl. No.: 273,714

[22] Filed: Nov. 17, 1988

Related U.S. Application Data

[63] Continuation of Ser. No. 729,354, May 1, 1985, abandoned.

[30] Foreign Application Priority Data

May 2, 1984 [JP] Japan ............................. 59-089129

[51] Int. Cl.$^5$ ............................. G02B 3/00; G02B 6/00
[52] U.S. Cl. ................................. 350/432; 350/96.18; 350/96.24
[58] Field of Search ................... 350/432, 96.10, 96.18, 350/96.24; 362/32

[56] References Cited

U.S. PATENT DOCUMENTS

| 4,101,196 | 7/1978 | Imai .................... 350/96.25 |
| 4,113,354 | 9/1978 | Yamasita et al. .......... 350/286 |
| 4,266,534 | 5/1981 | Ogawa ..................... 362/32 |
| 4,415,240 | 11/1983 | Nishioka et al. . |
| 4,443,069 | 4/1984 | Mihara ................... 350/432 |
| 4,548,480 | 10/1985 | Yamamoto et al. ........... 350/432 |
| 4,620,773 | 11/1986 | Fukuda ................... 350/432 |

FOREIGN PATENT DOCUMENTS 3148599 6/1982 Fed. Rep. of Germany .
57-170701 10/1982 Japan .

Primary Examiner—P. M. Dzierzynski
Attorney, Agent, or Firm—Cushman, Darby & Cushman

[57] ABSTRACT

An illumination optical system for endoscopes wherein, in order to make it possible to make an illumination of a uniform and sufficient brightness over a wide range of the surface of an object to be observed, a cover lens arranged in front of the exit end face of a light guide is so formed that its surface on the object side may be a convex aspherical surface or may be a convex spherical surface or may have a concave center part and larger in the refractive index in the peripheral part than in the center part. The light guide may be a light emitting device.

20 Claims, 4 Drawing Sheets

ILLUMINATION OPTICAL SYSTEM FOR ENDOSCOPES

This is a continuation of application Ser. No. 729,354, filed May 1, 1985, now abandoned.

BACKGROUND OF THE INVENTION (a) Field of the Invention:

The present invention relates to an illumination optical system for endoscopes.

(b) Description of the Prior Art:

In this kind of conventional illumination optical system for endoscopes, generally a cover lens is arranged in front of the exit end face of a light guide, that is, on the object side so as to diffuse the light emitted out of the light guide over a wide range. However, there have been problems that the light emitted at a wide angle out of the exit end face of the light guide will be turbulently reflected to vanish on the inner surface of the outer peripheral part of the cover lens or will be totally reflected on the inner surface of said outer peripheral part so as to be directed to the visual field center part or light guide and therefore the delivery of the light to the peripheral part of the visual field will be insufficient to obtain a uniform illumination over a wide range. Therefore, in order to solve such problems, there has been invented such endoscope optical system as is mentioned, for example, in Japanese U.M. Preliminary Publication No. Sho No. 57-170701 wherein the surface on the light guide side of a cover lens (concave lens) is made a compound surface consisting of a spherical center part and a conical peripheral part. However, therein, the direction of the principal ray of the light emitted at a wide angle out of the exit end face of the light guide is only changed but the total reflection on the inner surface of the outer peripheral part of the cover lens of the lower side ray is not yet solved. Therefore, it has been insufficient to obtain a uniform illumination over a wide range.

SUMMARY OF THE INVENTION

A primary object of the present invention is to provide an illumination optical system for endoscopes wherein an illumination of a uniform and sufficient brightness can be made over a wide range.

According to the present invention, this object is attained by forming the surface on the object side of a cover lens to be convex aspherical as directed to the object to be illuminated so as to be hard for the light entering the cover lens to be turbulently reflected into the interior or totally reflected on the outer peripheral surface.

According to a preferred formation of the present invention, the cover lens is a negative lens wherein the curvature of the peripheral part of the object side surface is larger than that of its center part.

According to another preferred formation of the present invention, the cover lens is a positive lens formed as an inhomogeneous medium lens wherein the refractive index of the peripheral part is larger than that of the center part. Thereby, the height of ray will be lower and the light will be hardly cut. In this case, the curvature of the peripheral part of the object side surface of said cover lens may be smaller than that of its center part.

The above mentioned object can be attained also by forming the surface on the object side of a cover lens to be a convex spherical surface so as to be an inhomogeneous medium lens wherein the refractive index of the peripheral part is larger than that of the center part.

This and other objects of the present invention will become more apparent during the course of the following detailed description and appended claims.

DESCRIPTION OF THE PREFERRED EMBODIMENTS

Figure 1:
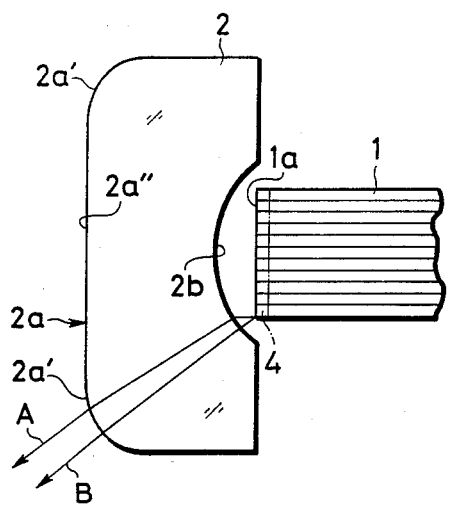
FIG. 1 is a formation view of an embodiment of the illumination optical system for endoscopes according to the present invention.
Figure 2:
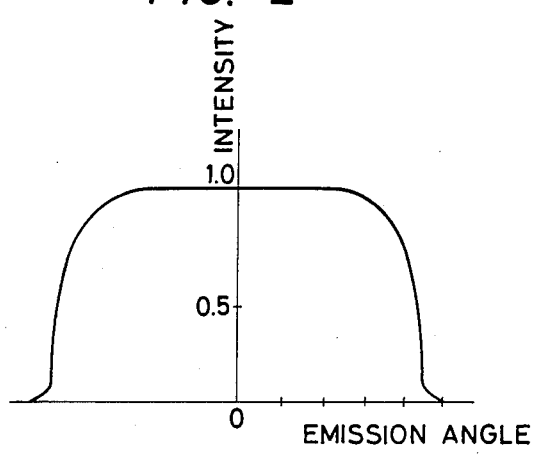
FIG. 2 is a distribution curve of the luminous intensity of the embodiment in FIG. 1.

The present invention shall be explained in detail in the following on the basis of the embodiment shown in FIG. 1. The reference numeral 1 represents a light guide and 2 represents a cover lens which is a negative lens which is arranged in front (on the object side) of the exit end face 1a of the light guide 1 and of which the surface 2a on the object side is formed to be a convex aspherical surface consisting of an aspherical (large curvature) peripheral part 2a' and a plane (0 curvature) center part 2a'' and the surface 2b on the light guide 1 side is formed to be a concave spherical surface. Therefore, the principal ray A and lower ray B of the light emitted at a wide angle out of the exit end face 1a of the light guide 1 will pass through the aspherical peripheral part 2a' to illuminate the peripheral part of the visual field and will not be turbulently or totally reflected on the inner surface of the outer peripheral part of the cover lens 2. As a result, such substantially trapezoidal distribution curve of the luminous intensity as is shown in FIG. 2 will be obtained and a uniform illumination over a wide range will be able to be well obtained.

Figure 3:
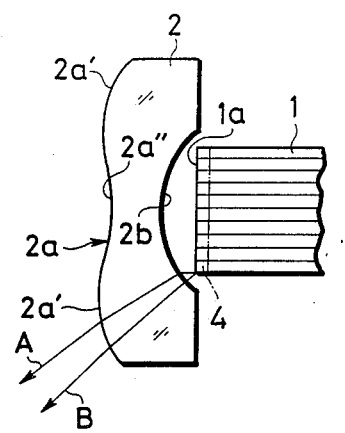
FIGS. 3 to 15 are respective formation views of the second to fourteenth embodiments.

FIG. 3 shows the second embodiment in which the center part 2a'' of the surface 2a on the object side of the cover lens 2 is formed to be a concave surface but the other formation is the same as in the above mentioned first embodiment.

Figure 4:
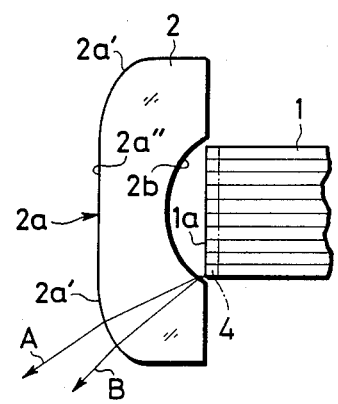

FIG. 4 shows the third embodiment in which the surface 2b on the light guide 1 side of the cover lens 2 is formed to be an aspherical surface so that the degree of diffusion of the light emitted at a wide angle out of the exit end face 1a of the light guide 1 may be reduced to save the lower ray B and the outside diameter of the cover lens 2 may well be smaller than in the above mentioned first embodiment but the other formation is the same as in the above mentioned first embodiment.

Figure 5:
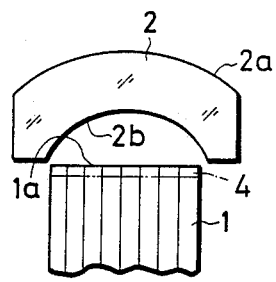

FIG. 5 shows the fourth embodiment in which the surface 2a on the object side of the cover lens 2 is formed to be a convex spherical surface and the surface 2b on the light guide 1 side of the cover lens 2 is formed to be a concave aspherical surface to form the entirety as a negative lens.

Figure 6:
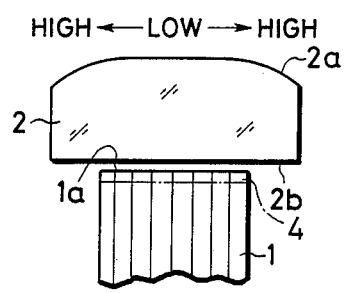

FIG. 6 shows the fifth embodiment in which the surface 2a on the object side of the cover lens 2 is formed to be a convex aspherical surface and the surface 2b on the light guide 1 side of the cover lens 2 is formed to be a plane to form an inhomogeneous medium lens wherein the refractive index is higher in the peripheral part than in the center part so as to have a function as of a negative lens.

Figure 7:
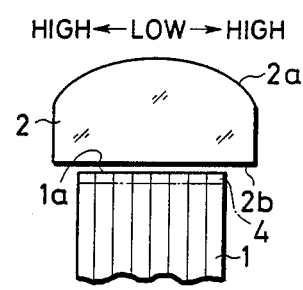

FIG. 7 shows the sixth embodiment in which the surface 2a on the object side of the cover lens 2 is formed to be a convex spherical surface but the other formation is the same as in the above mentioned fifth embodiment.

Figure 8:
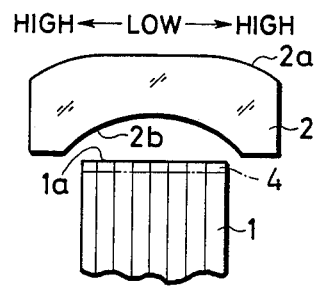

FIG. 8 shows the seventh embodiment in which the cover lens 2 which is a negative lens is formed of an inhomogeneous medium lens higher in the refractive index in the peripheral part than in the center part so as to direct the light emitted out of the center part of the exit end face 1a of the light guide 1 more to the peripheral part, the surface 2a on the object side is formed to be the same convex aspherical surface as in the first embodiment and the surface 2b on the light guide 1 side is formed to be a concave spherical surface or concave aspherical surface.

Figure 9:
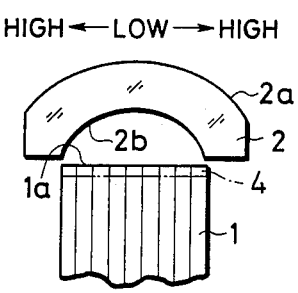

FIG. 9 shows the eighth embodiment in which the cover lens 2 which is a negative lens is formed of an inhomogeneous medium lens higher in the refractive index in the peripheral part than in the center part so as to direct the light emitted out of the center part of the exit end face 1a of the light guide 1 more to the peripheral part. This embodiment is different from the seventh embodiment in respect that the object side surface is formed to be a convex sperical surface.

In each of the above mentioned fifth to eighth embodiments, the course of the ray passing through the cover lens 2 which is an inhomogeneous medium concave lens will be a curve gradually curving toward the peripheral part, therefore the ray height in the course will become lower than in such case that the course of the ray is a straight line as in a homogeneous medium negative lens and, as a result, there is an advantage that an eclipse will be hard to occur.

Figure 10:
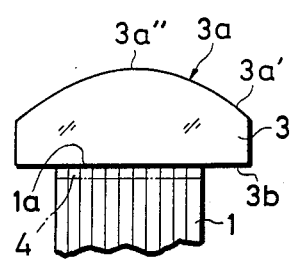

FIG. 10 shows the ninth embodiment in which the cover lens 3 is formed as a positive lens of which the surface 3a on the object side is formed to be a convex aspherical surface consisting of a peripheral part 3a' small in the curvature and a center part large in the curvature and the surface 3b on the light guide 1 side is formed to be a plane.

Figure 11:
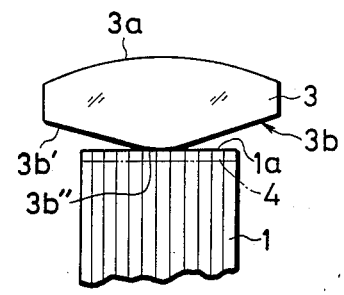

FIG. 11 shows the tenth embodiment in which the surface 3a on the object side of the cover lens 3 is formed to be a convex spherical surface or convex aspherical surface and the surface 3b on the light guide 1 side is formed as a convex aspherical surface consisting of a peripheral part 3b' small in the curvature and a center part 3b'' large in the curvature.

Figure 12:
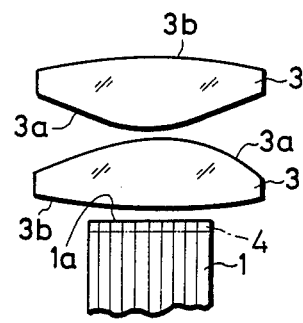

FIG. 12 shows the eleventh embodiment in which cover lenses 3, 3 which are two convex lenses of which the surface 3a of one is formed to be a convex aspherical surface consisting of a peripheral part small in the curvature and a center part large in the curvature and the surface 3b of the other is formed to be a convex spherical surface or convex aspherical surface are overlapped in the axial direction so that the surfaces 3a may be opposed to each other.

In each of the above mentioned ninth to eleventh embodiments, the cover lens 3 which is a positive lens will be smaller in the curvature in the peripheral part than in the center part and will be smaller in the angle of expansion after the ray is once converged and, as a result, there is an advantage that the eclipse of the ray will be able to be prevented.

Figure 13:
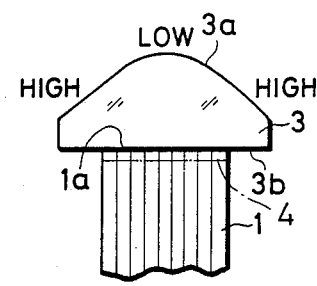

FIG. 13 shows the twelfth embodiment in which the cover lens 3 which is a positive lens is formed of an inhomogeneous lens higher in the refractive index in the peripheral part than in the center part so as to direct the light emitted out of the center part of the exit end face 1a of the light guide 1 toward the peripheral part but the other formation is the same as in the ninth embodiment.

Figure 14:
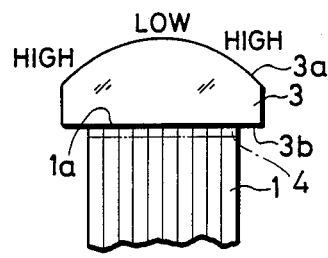

FIG. 14 shows the thirteenth embodiment in which the surface 3a on the object side of the cover glass 3 is formed to be a convex spherical surface but the other formation is the same as in the twelfth embodiment.

Figure 15:
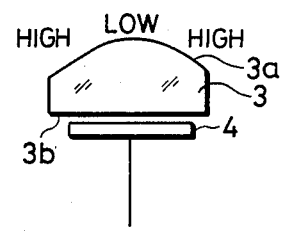

FIG. 15 shows the fourteenth embodiment in which such light emitting device 4 as an LED is used in place of the light guide 1 in the twelfth embodiment. It is needless to say that such light emitting device 4 can be used in place of the light guide 1 in the above mentioned other embodiments as shown by the chain line in the respective embodiments. Such formation is adapted for endoscopes of which the tip part is movable.

In each of the above mentioned twelfth and thirteenth embodiments, the course of the ray passing through the cover lens 3 which is an inhomogeneous medium positive lens will be a curve gradually curving toward the peripheral part, therefore the ray height in the course will become lower than in such case that the course of the ray is a straight line as in a homogeneous medium positive lens and, as a result, there is an advantage that an eclipse will be harder to occur.

By the way, the above mentioned cover lenses 2 and 3 are preferably made by glass molding or plastic molding and, as a result, are easy to make.

Figure 16:
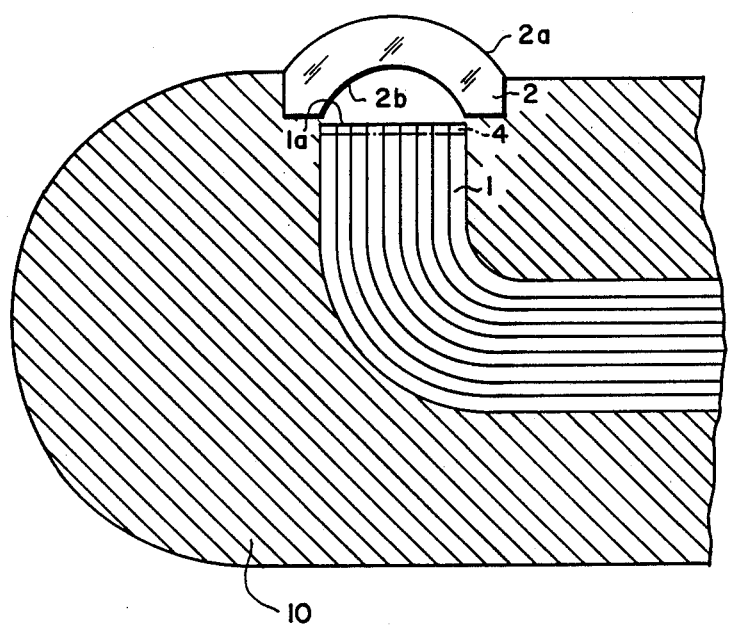
FIG. 16 is an elevational view partly in cross-section and partly broken away for clarity showing the embodiment of FIG. 9 within the end of an otherwise conventional endoscope.

Referring to FIG. 16, the embodiment of FIG. 9 is shown, by way of example, schematically within the end portion of a conventional endoscope 10. The particular endoscope structure in which the illumination optical system provided in accordance with the present invention is mounted, however, can be any endoscope known in the art. Further, the particular embodiment of the present invention to be provided in a particular endoscope structure is deemed to be dependent upon the intended use of the endoscope and, therefore, will be readily apparent to the ordinary artisan upon a review of this application.

As described above, the illumination optical system for endoscopes according to the present invention has a practically important advantage that a uniform illumination over a wide range can be well obtained.

What is claimed is:

1. An illumination optical system for endoscopes comprising a fiber bundle having an exit end face and emitting light from said exit end face and a cover lens arranged in front of the exit end face of said fiber bundle so that the light emitted from the exit end face of said fiber bundle is irradiated toward an object to be observed by an endoscope in order to illuminate the object to be observed by the endoscope through said cover lens, said cover lens consisting of at most two lens elements arranged along an optical axis of said illumination optical system, each of said at most two lens elements being composed of an inhomogeneous medium in which the refractive index of a peripheral part distant from the optical axis of said illumination optical system is larger than that of a center part close to the optical axis, wherein said cover lens has negative refractive power as a whole and each of said at most two lens elements is provided with a convex spherical surface, toward the object, on the side of the object.

2. An illumination optical system for endoscopes comprising a fiber bundle having an exit end face and emitting light from said exit end face and a cover lens arranged in front of the exit end face of said fiber bundle so that the light emitted from the exit end face of said fiber bundle is irradiated toward an object to be observed by an endoscope in order to illuminate the object to be observed by the endoscope through said cover lens, said cover lens consisting of at most two lens elements arranged along an optical axis of said illumination optical system, each of said at most two lens elements being composed of an inhomogeneous medium in which the refractive index of a peripheral part distant from the optical axis of said illumination optical system is larger than that of a center part close to the optical axis, wherein said cover lens has positive refractive power as a whole and each of said at most two lens elements is provided with a convex spherical surface, toward the object, on the side of the object.

3. An illumination optical system for endoscopes comprising a fiber bundle having an exit end face and emitting light from said exit end face and a cover lens arranged in front of the exit end face of said fiber bundle so that the light emitted from the exit end face of said fiber bundle is irradiated toward an object to be observed by an endoscope in order to illuminate the object to be observed by the endoscope through said cover lens, said cover lens consisting of at most two lens elements arranged along an optical axis of said illumination optical system, each of said at most two lens elements being composed of an inhomogeneous medium in which the refractive index of a peripheral part distant from the optical axis of said illumination optical system is larger than that of a center part close to the optical axis, wherein each of said at most two lens elements is provided with a convex aspherical surface, toward the object, on the side of the object.

4. An illumination optical system for endoscopes comprising a fiber bundle having an exit end face and emitting light from said exit end face and a cover lens arranged in front of the exit end face of said fiber bundle so that the light emitted from the exit face of said fiber bundle is irradiated toward an object to be observed by an endoscope in order to illuminate the object to be observed by the endoscope through said cover lens, said cover lens consisting of at most two lens elements arranged along an optical axis of said illumination optical system, wherein said cover lens has negative refractive power as a whole and each of said at most two lens elements is provided with a concave surface on the side of the exit end face of said fiber bundle and a smooth aspherical surface on the side of the object and has negative refractive power, said aspherical surface being formed so that the curvature of a peripheral part distant from the optical axis of said illumination optical system is larger than that of a center part close to the optical axis.

5. An illumination optical system for endoscopes according to claim 4, wherein said object side surface has a convex shape toward the object.

6. An illumination optical system for endoscopes according to claim 4, wherein said object side surface has a concave shape in the center part toward the object and a convex shape in the peripheral part toward the object.

7. An illumination optical system for endoscopes according to claim 4, wherein said exit end face side surface is formed as a smooth aspherical surface.

8. An illumination optical system for endoscopes according to claim 7, wherein said exit end face side surface is formed so that the curvature of the peripheral part distant from the optical axis of said illumination optical system is smaller than that of the center part close to the optical axis.

9. An illumination optical system for endoscopes according to claim 4, wherein said exit end face side surface is formed as a spherical surface.

10. An illumination optical system for endoscopes according to claim 4, wherein said object side surface is formed as a plane surface in the center part and has a convex shape in the peripheral part toward the object.

11. An illumination optical system for endoscopes comprising a fiber bundle having an exit end face and emitting light from said exit and face and a cover lens arranged in front of the exit end face of said fiber bundle as that the light emitted from the exit end face of said fiber bundle is irradiated toward an object to be observed by an endoscope in order to illuminate the object to be observed by an endoscope through said cover lens, said cover lens consisting of at most two lens elements arranged along an optical axis of said illumination optical system, among lens surfaces of which, a surface nearest the object is formed as a convex spherical surface toward the object and a surface nearest the exit end face of said fiber bundle is formed as a smooth convex aspherical surface toward the object.

12. An illumination optical system for endoscopes according to claim 11, wherein said exit end face side surface is formed so that the curvature of the peripheral part distant from the optical axis of said illumination optical system is smaller than that of the center part close to the optical axis.

13. An illumination optical system for endoscopes, comprising a fiber bundle having an exit end face and emitting light from said exit end face and a cover lens arranged in front of the exit end face of said fiber bundle so that the light emitted from the exit face of said fiber bundle is irradiated toward an object to be observed by an endoscope in order to illuminate the object to be observed by the endoscope through said cover lens, said cover lens consisting of at most two lens elements arranged along an optical axis of said illumination optical system, among lens surfaces of which, a surface nearest the object is formed as a smooth aspherical surface and the other surfaces are each formed as a smooth surface, wherein said cover lens has positive refractive power as a whole and each of said at most two lens elements is provided with a convex aspherical surface, toward the object, on the side of the object, and has positive refractive power, said aspherical surface being formed so that the curvature of a peripheral part distant from the optical axis of said illumination optical system is smaller than that of a center part close to the optical axis.

14. An illumination optical system for endoscopes according to claim 13, wherein each of said at most two lens elements in provided with a plane surface on the side of the exit face of said fiber bundle.

15. An illumination optical system for endoscopes according to claim 13, wherein each of said at most two lens elements is provided with a smooth aspherical surface on the side of the exit end face of said fiber bundle, said aspherical surface being formed as that the curvature of the peripheral part distant from the optical axis of said illumination is smaller than that of the center part close to the optical axis.

16. An illumination optical system for endoscopes comprising a fiber bundle having an exit end face and emitting light from said exit end face and a cover lens arranged in front of the exit end face of said fiber bundle so that the light emitted from the exit end face of said fiber bundle is irradiated toward an object to be observed by an endoscope in order to illuminate the object to be observed by an endoscope through said cover lens, said cover lens consisting of at most two lens elements arranged along an optical axis of said illumination optical system, among lens surfaces of which, a surface nearest the object is formed as a convex spherical surface toward the object and a surface nearest the exit end face is formed as a smooth convex aspherical surface toward the exit end face, said aspherical surface being formed so that the curvature of a peripheral part distant from the optical axis of said illumination is smaller than that of a center part close to the optical axis.

17. The invention according to any on of claims 4—16, wherein said cover lens is formed as an inhomogeneous medium lens in which the refractive index of the peripheral part is larger than that of the center part.

18. An illumination optical system for endoscopes comprising a fiber bundle having an exit end face and emitting light from said exit end face and a cover lens arranged in front of the exit end face of said fiber bundle so that the light emitted from the exit end face of said fiber bundle is irradiated toward an object to be observed by an endoscope in order to illuminate the object to be observed by an endoscope through said cover lens, said cover lens consisting of two positive lenses arranged so that their convex surfaces are directed to each other along an optical axis, said two convex surfaces are each formed as a smooth aspherical surface.

19. The invention according to claim 18, wherein at least one of the aspherical surfaces of said two positive lenses is formed so that the curvature of the peripheral part distant from the optical axis of said illumination optical system is smaller than that of the center part close to the optical axis.

20. The invention according to claim 18 or 19, wherein at least one of said two cover lenses is formed as an inhomogeneous medium lens in which the refractive index of the peripheral part is larger than that of the center part.

* * * * *